US00PP11990P2

(12) United States Plant Patent
Zaiger et al.

(10) Patent No.: US PP11,990 P2
(45) Date of Patent: Jul. 17, 2001

(54) INTERSPECIFIC TREE NAMED 'FLAVORFALL'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/249,565

(22) Filed: Feb. 8, 1999

(51) Int. Cl.[7] ..... A01H 5/00
(52) U.S. Cl. ..... Plt./184
(58) Field of Search ..... Plt./184, 180, 185

(56) References Cited

U.S. PATENT DOCUMENTS

P.P. 8,471 * 11/1993 Zaiger et al. ..... Plt./184

* cited by examiner

*Primary Examiner*—Bruce R. Campell
*Assistant Examiner*—Wendy C Baker

(57) ABSTRACT

A new and distinct variety of interspecific tree (*Prunus salicina*×(*Prunus salicina*×*Prunus armeniaca*)); the features of the tree and its fruit are characterized with the tree budded on Nemaguard rootstock (unpatented), grown on Hanford sandy loam soil with Storie Index rating 95, in USDA Hardiness Zone 9, near Modesto, Calif., and with standard commercial cultural fruit growing practices, such as pruning, thinning, spraying, irrigation and fertilization. Its novelty consists of the following unique combination of features that are desirable in a new interspecific tree:

1. Heavy and regular production of large size fruit.
2. Fruit ripening in the late maturity season.
3. Fruit with firm flesh, good storage and shipping quality.
4. Fruit with high soluble solids, averaging 17.4° Brix.
5. Relatively uniform size of fruit throughout the tree.
6. Fruit holding firm on the tree 14 to 18 days after maturity (shipping ripe).
7. Fruit with good flavor and eating quality.
8. Fruit with an attractive garnet red skin color.
9. Vigorous, upright growth.

1 Drawing Sheet

ORIGIN OF THE VARIETY

The new and distinct variety of interspecific Prunus tree (*Prunus salicina*×(*Prunus salicina*×*Prunus armeniaca*) was originated by us in our experimental orchard located near Modesto, Calif., as a cross between two selected seedlings with field identification numbers 65EC752 and 4G1180. The maternal parent (65EC752) originated from an open pollinated late maturing plum seedling selection of unknown parentage. The pollen parent (4G1180) originated as a plumcot from an open pollinated Red Beaut Plum (U.S. Plant Pat. No. 2,539) tree that had been grown from budwood, which had been irradiated with cobalt. A large group of these seedlings, growing on their own root, were planted and maintained under close and careful observation by us, during which time the present variety exhibited fruit with the desirable late maturing characteristic and was selected for asexual reproduction and commercialization.

ASEXUAL REPRODUCTION OF THE VARIETY

Asexual reproduction of the new and distinct variety of interspecific tree was by budding on Nemaguard rootstock (unpatented), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The present new and distinct variety of interspecific Prunus Sp. tree (plum×plumcot) is of large size, vigorous, upright growth, and a productive and regular bearer of large, yellow flesh, clingstone fruit with good flavor and eating quality. The fruit is further characterized by being relatively uniform in size throughout the tree, having firm flesh with good storage and shipping quality, having an attractive garnet red skin color, having high soluble solids (17.4° Brix), and ripening in the late maturity season. In comparison to the fruit of the late maturing interspecific tree Flavorich (U.S. Plant Pat. No. 8,546), the fruit of the present new variety is approximately 20 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Pruned approximately 12 to 14 feet in height and 12 to 14 feet in width, primarily for economical harvesting of fruit.

*Vigor.*—Vigorous. Tree growth the first growing season to approximately 6 to 7 feet in height and 4 to 5 feet in width. During the first dormant season the tree is pruned to 3 to 4 feet in height and primary scaffolds are selected.

*Growth.*—Upright growth habit, usually pruned to vase shape.

*Productivity.*—Productive. Fruit set is usually 1½ or more times needed for crop load. Fruit numbers are reduced and spaced by thinning to produce desired marketable size.

*Bearer.*—Regular. Produced adequate crop load for 5 consecutive years.

*Density.*—Medium dense. Pruned to vase shape by removing branches and leaves from the center to allow more sunlight to penetrate the center of the tree to enhance fruit color, improve Brix and to keep fruit wood healthy.

*Hardiness.*—Grown in USDA Hardiness Zone 9. Winter chilling requirement estimated to be 500 to 600 hours below 45° F.

Trunk:

*Size.*—Large. Average circumference of 21 inches at 9 inches above the ground on a 10 year old tree.

*Texture.*—Medium shaggy.

*Color.*—Brown to dark brown (6-E-5) to (6-F-5).

Branches:

*Size.*—Medium. Average circumference of 9 inches at 36 inches above the ground. Crotch angle varies from 30 to 45 degrees. Increases with heavy crop load.

*Texture.*—Smooth to medium rough. Texture gets rougher with age of growth.

*Lenticels.*—Average number of 30 in a 4 square inch section. Average length of 11/64 inch, average width of 3/64 inch. Color varies from tomato red to fox red (8-C-8) to (8-D-7).

*Color.*—Light brown to brown (5-E-5) to (5-D-6), getting darker with age of growth.

Leaves:

*Size.*—Large. Average length 4½ inches. Average width 1⅝ inches.

*Form.*—Oblanceolate. Pointed.

*Margin.*—Serrate.

*Thickness.*—Medium.

*Surface.*—Smooth.

*Petiole.*—Medium length average ¾ inch. Medium thickness average 3/32 inch. Color — yellowish green to grayish green (8-C-8) to (8-D-7). Grooved longitudinally.

*Glands.*—Globose. Number varies from 2 to 5. Average number 2. Size medium, average diameter 1/64 inch. Color varies from henna to brown (7-E-8) to (7-E-7). Located on base of leaf blade and upper portion of petiole.

*Color.*—Upper surface — green to deep green (28-F-6) to 28-F-8). Lower surface — light green to spinach green (28-E-5) to (28-E-6).

Flower buds:

*Size.*—Medium. Average length ½ inch. Average diameter 19/64 inch.

*Form.*—Plump, conical, becoming elongated near maturity.

Flowers:

*Size.*—Medium. Average diameter ¾ inch. Average length 35/64.

*Petal.*—Number — 5. Shape — Obovate, edges vary from smooth to slightly scalloped. Average length 31/64 inch. Average width 23/64 inch.

*Sepals.*—Number — 5. Alternately arranged to petals. Shape — Ovate to obovate. Average length 5/32 inch. Average width ⅛ inch. Color — green (29-D-7) to (29-D-8).

*Stamens.*—Number of stamens varies from 24 to 30. Average length 7/16 inch. Filament color — white (1-A-1). Anther color — orange (6-A-7).

*Pollen.*—Present. Self sterile — requires pollenizer.

*Pistil.*—Usually one. Average length 31/64 inch. Color — pastel yellow (2-A-4).

*Aroma.*—Slight fragrance.

*Bloom period.*—Date of First Bloom — Feb. 20, 1997. Date of Last Bloom — Feb. 27, 1997. Varies slightly with climatic conditions.

*Color.*—White (1-A-1).

Fruit:

*Maturity when described.*—Shipping ripe.

*Date of first picking.*—Oct. 5, 1997.

*Date of last picking.*—Oct. 10, 1997. Varies slightly with climatic conditions.

*Size.*—Large. Average diameter axially 2⅜ to 2½ inches. Average diameter transversely in suture plane 2⅜ to 2½ inches. Average weight 181 grams, varies from 172 to 198 grams. Varies with number of fruit on tree, climatic conditions and cultural practices.

*Form.*—Globose, nearly rounded, slightly retuse at stem end.

*Suture.*—Very shallow, extends from base to apex.

*Ventral surface.*—Nearly rounded, some fruit slightly lipped near point of stem attachment.

*Apex.*—Usually rounded, varies from rounded to slight apical tip.

*Base.*—Retuse.

*Cavity.*—Rounded to slightly elongated in suture plane. Average depth ⅜ inch. Average breadth ½ inch.

Flesh:

*Ripens.*—Evenly.

*Texture.*—Firm.

*Fibers.*—Few, very small, tender.

*Aroma.*—Very slight.

*Amygdalin.*—Undetected.

*Eating quality.*—Good.

*Flavor.*—Good.

*Juice.*—Moderate, good balance between sugar and acid, enhances flavor. Average Brix 17.4°.

*Color.*—Light yellow to maize yellow (4-A-5) to (4-A-6). Pit cavity — cinnamon brown to light brown (6-D-6) to (6-D-8).

Stem:

*Size.*— ½ to ⅝ inch in length. 3/32 to ⅛ inch in width.

*Color.*—Light green to pea green (29-D-4) to (29-D-6).

Skin:

*Thickness.*—Medium.

*Texture.*—Medium, tenacious to the flesh.

*Bloom.*—Moderate to heavy bloom.

*Tendency to crack.*—None.

*Color.*—Light yellow to light orange 4-A-5) to (5-A-4) ground color. Overspread with Madder red to Garnet red (11-B-8) to (11-E-8) except in very small areas, randomly spaced, showing a very light speckling of yellow ground color in some areas of the skin, primarily toward the base of the fruit.

Stone:

*Type.*—Clingstone.

*Size.*—Medium. Average length 1⅛ inches. Average width ¾ inch. Average thickness ⅜ inch.

*Form.*—Obovate.

*Base.*—Retuse. Portions of the stone extending beyond stem attachment on each side of stem leaving the base of the stone slightly retuse.

*Apex.*—Acuminate.

*Surface.*—Lightly pitted throughout, two narrow ridges on each side of suture from base to apex. Short ridges extending from base toward apex approximately ⅓ length of the stone.

*Sides.*—Equal to unequal. Unequal stones with suture extending further from center line between base and apex.

*Tendency to split.*—None.

*Color.*—Grayish orange to brownish orange (5-B-5) to (5-B-6).

Use: Dessert. Market — local and long distance.

Keeping quality: Good. Remains firm on tree for 14 to 18 days after maturity (shipping ripe). Stores well in cold storage for 3 weeks with no internal breakdown of flesh.

Shipping quality: Good. Packing and shipping trials gave minimal flesh bruising or skin scarring.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific Prunus Sp. tree, substantially as illustrated and described, characterized by its large size, vigorous, upright growth and a productive and regular bearer of large, late maturing, yellow flesh, clingstone fruit with good flavor and eating quality; the fruit is further characterized by having firm flesh, good shipping and storage quality, holding firm on the tree 14 to 18 days after maturity (shipping ripe), having an attractive garnet red skin color and, in comparison to the fruit of late maturing interspecific tree Flavorich (U.S. Plant Pat. No. 8,546), the fruit of the present variety is approximately 20 days later in maturity.

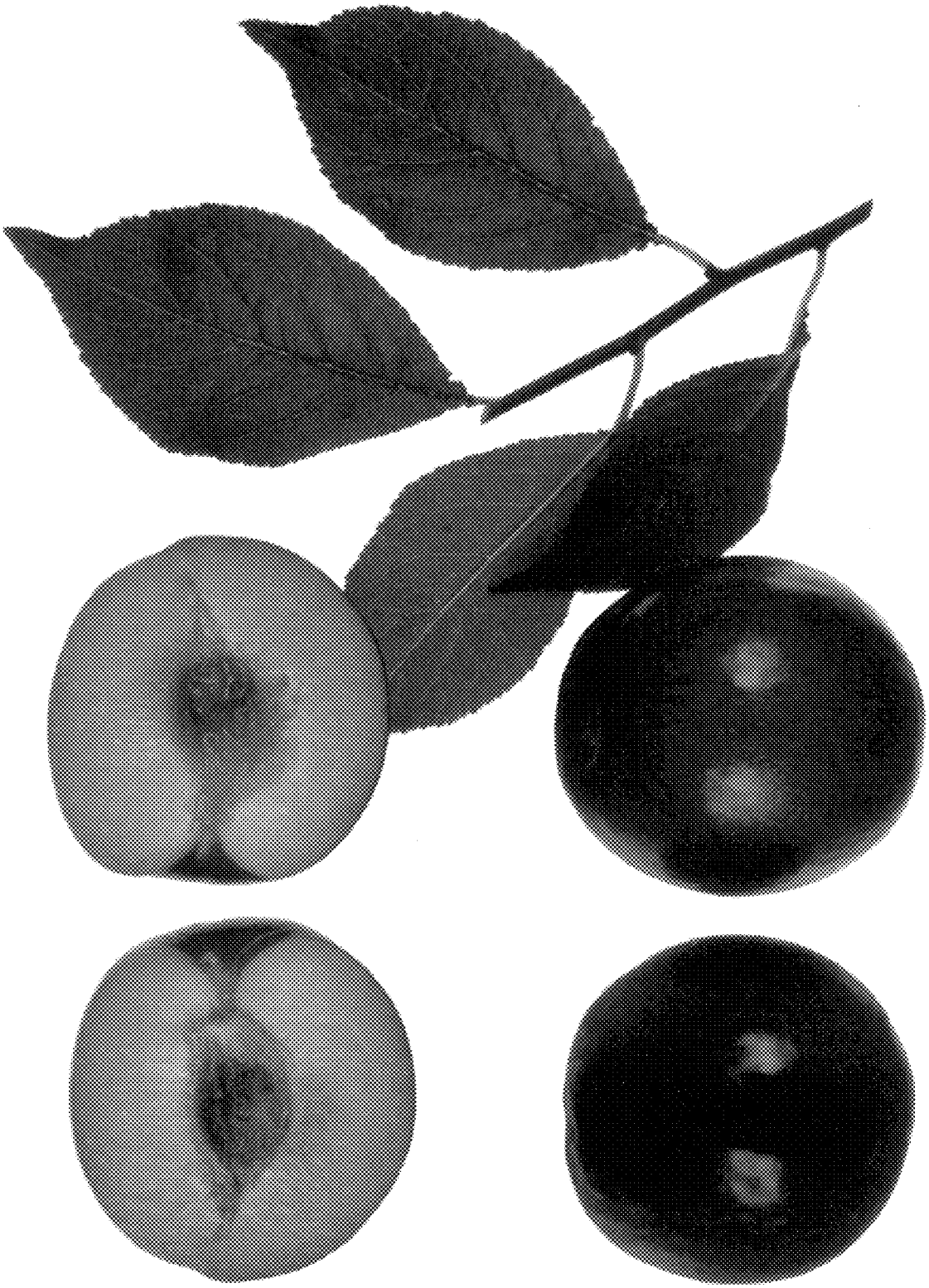

* * * * *